United States Patent
Ousdigian et al.

(10) Patent No.: US 6,892,094 B2
(45) Date of Patent: May 10, 2005

(54) COMBINED ANTI-TACHYCARDIA PACING (ATP) AND HIGH VOLTAGE THERAPY FOR TREATING VENTRICULAR ARRHYTHMIAS

(75) Inventors: Kevin T. Ousdigian, Shoreview, MN (US); Vasant Padmanabhan, Maple Grove, MN (US); Paul J. DeGroot, Brooklyn Park, MN (US); Walter H. Olson, North Oaks, MN (US); Vinod Sharma, Roseville, MN (US); Cameron J. Kaszas, Minneapolis, MN (US); Paul G. Krause, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 396 days.

(21) Appl. No.: 10/137,517

(22) Filed: Apr. 30, 2002

(65) Prior Publication Data

US 2003/0204210 A1 Oct. 30, 2003

(51) Int. Cl.[7] .............................................. A61N 1/39
(52) U.S. Cl. ........................................................ 607/4
(58) Field of Search .................................... 607/4–5, 7

(56) References Cited

U.S. PATENT DOCUMENTS

| | | | |
|---|---|---|---|
| 4,403,614 A | 9/1983 | Engle et al. | 128/419 D |
| 4,407,288 A | 10/1983 | Langer et al. | 128/419 PG |
| 4,428,378 A | 1/1984 | Anderson et al. | 128/419 PG |
| 4,821,723 A | 4/1989 | Baker, Jr. et al. | 128/419 D |
| 4,865,036 A | 9/1989 | Chirife | 128/419 D |
| 4,869,252 A | 9/1989 | Gilli | 128/419 PG |
| 4,949,719 A | 8/1990 | Pless et al. | 128/419 D |
| 4,967,747 A | 11/1990 | Carroll et al. | 128/419 D |
| 5,048,521 A | 9/1991 | Pless et al. | 128/419 PG |
| 5,107,850 A | 4/1992 | Olive | 128/705 |
| 5,161,527 A | 11/1992 | Nappholz et al. | 128/419 PG |
| 5,163,427 A | 11/1992 | Keimel | 128/419 D |
| 5,176,137 A | 1/1993 | Erickson et al. | 128/419 D |
| 5,191,884 A | 3/1993 | Gilli et al. | 128/419 D |
| 5,193,536 A | 3/1993 | Mehra | 128/419 D |
| 5,205,583 A | 4/1993 | Henseler et al. | 280/743 |
| 5,209,229 A | 5/1993 | Gilli | 128/419 D |
| 5,251,624 A | 10/1993 | Bocek et al. | 607/6 |
| 5,318,591 A | 6/1994 | Causey, III et al. | 607/5 |
| 5,330,505 A | 7/1994 | Cohen | 607/6 |
| 5,458,619 A | 10/1995 | Olson | 607/4 |
| 5,662,688 A | 9/1997 | Haefner et al. | 607/5 |
| 5,713,924 A * | 2/1998 | Min et al. | 607/4 |
| 5,855,893 A | 1/1999 | Weinkauf et al. | 424/195.1 |
| 5,913,535 A | 6/1999 | Taguchi et al. | 280/729 |
| 5,913,550 A | 6/1999 | Watanuki | 29/603.1 |
| 5,951,592 A * | 9/1999 | Murphy | 607/4 |
| 6,167,308 A | 12/2000 | DeGroot | 607/14 |
| 6,178,350 B1 | 1/2001 | Olson et al. | 607/4 |
| 6,230,055 B1 * | 5/2001 | Sun et al. | 607/5 |
| 6,442,426 B1 * | 8/2002 | Kroll | 607/4 |
| 6,493,579 B1 * | 12/2002 | Gilkerson et al. | 607/5 |
| 2003/0083703 A1 * | 5/2003 | Zhu et al. | 607/14 |

FOREIGN PATENT DOCUMENTS

EP    0 599 588    6/1994    ............ A61N/1/39

* cited by examiner

*Primary Examiner*—Carl H. Layno
(74) *Attorney, Agent, or Firm*—Michael C. Soldner; Girma Wolde-Michael

(57) ABSTRACT

A system and method for treating an arrhythmia of the heart, involves delivery of anti-tachy pacing (ATP) pulses to the heart, possibly followed by the delivery of a high-voltage shock. ATP delivery is controlled such that the time delivery of any high-voltage shock is not affected by the prior delivery of the ATP pulses. System control may be accomplished using one or more programmable parameters, which may include a user-specified shock energy.

50 Claims, 11 Drawing Sheets

COMBINED ANTI-TACHYCARDIA PACING (ATP) AND HIGH VOLTAGE THERAPY FOR TREATING VENTRICULAR ARRHYTHMIAS

FIELD OF THE INVENTION

The present invention relates generally to implantable cardioverters (ICDs); and more particularly, the present invention relates to a system and method for delivering appropriate therapies to treat various tachycardia conditions.

BACKGROUND OF THE INVENTION

Implantable cardioverter-defibrillator (ICD) art has long distinguished ventricular arrhythmias (VAs) by rate and type. Ventricular Tachycardias (VTs) generally are those arrhythmias with rates between 150 and 250 bpm. These rhythms can be further differentiated by their ECG configuration as either monomorphic or polymorphic. Arrhythmias with rates above the upper VT range are typically classified as Ventricular Fibrillation (VF).

To treat each type of arrhythmia in the appropriate manner, some ICDs are equipped with "tiered therapies" for delivering therapy based on the type of arrhythmia detected by the device. Such devices, often referred to as Implantable Cardioverter-Defibrillators (ICDs), generally differentiate arrhythmias by rate. For example, less dangerous arrhythmias such as VTs may be treated by delivering a series of low-power, relatively high-rate, pacing pulses to the heart. This therapy is often referred to as anti-tachyarrhythmia pacing therapy (ATP). In contrast, more perilous arrhythmias such as VFs are often treated using a more aggressive shock therapy. For example, many ICDs may be programmed to first treat a VT with low-power ATP. If ATP fails to terminate the VT or the VT progresses to ventricular fibrillation, the device may then deliver one or more high-power cardioversion or defibrillation shocks.

As may be apparent from the foregoing discussion, some types of arrhythmias are better treated with high-voltage shocks than ATP therapy. For this reason, high-voltage shocks may be "over-used" to treat conditions that could otherwise be successfully treated using ATP. The more aggressive treatment is prescribed because most clinicians prefer a fast termination of the arrhythmia rather than allowing time to pass while a determination is made as to whether ATP therapy will terminate the rhythm. This tendency to utilize a more aggressive therapy is intended to reduce the possibility of patient syncope. However, this rationale results in some patients unnecessarily enduring the pain of a high-voltage shock when painless ATP therapy could have successfully terminated the rhythm. A good example of this over-aggressive therapy selection involves monomorphic VTs having rates above 200 bpm. These VTs are often treated by high-energy shocks when, in fact, they may generally be terminated by low-energy ATP therapy.

Preventing the unnecessary delivery of high-voltage shocks has long been recognized as a very desirable goal. As a result, monitoring the rhythm during the charging of the high-voltage capacitors in preparation for shock delivery has been proposed. For example in U.S. Pat. No. 4,949,719, issued to Pless et al, and U.S. Pat. No. 5,191,884 issued to Gilli et al, the implanted device monitors heart rhythm during charging to determine whether the arrhythmia has spontaneously terminated, and thereafter aborts the charging of the output capacitors if the rhythm has returned to normal. Another approach to this issue is found in U.S. Pat. No. 5,318,591, issued to Causey et al., and incorporated herein by reference in its totality. The '591 patent teaches a three-tiered progressive therapy approach using ATP as a first recourse, followed by delivery of a cardioversion pulse in the event ATP failed, with a defibrillation shock to be delivered if cardioversion is unsuccessful. The ICD begins charging its high-powered capacitors in parallel with the application of the ATP therapy. In addition, this charging may also start in parallel with the verification interval immediately following the previous therapy, during which time the ICD attempts to verify arrhythmia termination.

Numerous other patents describe ATP pacing including U.S. Pat. No. 5,193,536, issued to Mehra, U.S. Pat. No. 5,458,619 issued to Olson, U.S. Pat. No. 6,167,308, issued to DeGroot, and U.S. Pat. No. 6,178,350, issued to Olson, et al. Other patents describe in more detail systems that analyze the sequence and timing of events prior to the selection of a therapy. Such patents include U.S. Pat. No. 5,205,283 issued to Olson, U.S. Pat. No. 5,193,550 issued to Duffin, U.S. Pat. No. 5,193,535 issued to Bardy et al., U.S. Pat. No. 5,161,527 issued to Nappholz at al., U.S. Pat. No. 5,107,850 issued to Olive and U.S. Pat. No. 5,048,521, issued to Pless et al.

In the patents listed above, several basic strategies are generally followed. A first strategy is to associate each type of arrhythmia with a predetermined set of criteria. Next, a patient's heart rhythm is monitored to identify a heart event, including intervals and/or rates associated with the event. This information is then compared against the various criteria sets to analyze the likelihood that the event may be characterized as a specific type of arrhythmia. Monitoring continues until one of the criteria sets is met, resulting in detection and diagnosis of the arrhythmia. A second basic strategy involves defining a set of criteria for events, intervals, and rates that is generally indicative of a group of arrhythmias. After the criterion is met, the preceding and/or subsequent events are analyzed to determine which specific arrhythmia is present.

As is evident from a review of the above-cited references, many implantable anti-tachycardia pacemakers provide a variety of ATP regimens. Normally, these regimens are applied according to a pre-programmed sequence, such as burst or ramp therapies among others. Each therapy extends over a predetermined number of pacing pulses. After delivery of these pacing pulses, the devices generally determine whether the pulses were effective in terminating the detected arrhythmia episode as may be confirmed by a return to sinus rhythm. This is identified by detecting a sequence of spontaneous depolarizations separated by greater than a predefined interval. In the absence of detected termination, the ICD applies more aggressive therapies such as synchronized cardioversion pulses or defibrillation shocks. While the delivery of ATP in some cases makes shock therapy unnecessary, a further reduction in the delivery of high-voltage shocks is still desirable.

SUMMARY OF THE INVENTION

The present invention provides a system and method for treating an arrhythmia of the heart. The inventive system includes a first output circuit to deliver anti-tachy pacing (ATP) pulses to the heart, and a second output circuit to deliver a high-voltage shock. The system further includes a control circuit that controls the time of delivery of the ATP pulses relative to delivery of the high-voltage shock based on an adjustable parameter. Delivery of the ATP pulses is generally controlled so that the time of any subsequent delivery of the high-voltage shock is not affected by the prior delivery of the ATP pulses.

In one embodiment, a programmable value is used to indicate a charge energy for the high-voltage shock. This charge energy may be used, in turn, to determine the time required to charge one or more high-voltage capacitors included in the second output circuit. This charge time may then be used to determine whether enough time exists to deliver ATP therapy without affecting any subsequent delivery of a high-voltage shock.

In one embodiment, additional first and second parameters are used to control ATP and shock delivery. The first parameter indicates an amount of time required to deliver the ATP pulses, while a second parameter indicates an amount of time required to determine whether the ATP therapy terminated the arrhythmia. In this embodiment, ATP therapy is only delivered if the sum of the first and second parameters is not greater than the time required to charge the one or more high-voltage capacitors. Stated otherwise, ATP therapy is only delivered in a situation in which the ATP therapy delivery will not prolong the time to delivery of the shock.

The inventive system utilizes a "confirmation" period to determine whether the ATP therapy terminated the arrhythmia. In one embodiment, this confirmation period is initiated prior to the end of capacitor charging. In another embodiment, confirmation is initiated only after the end of capacitor charging to provide more time for the termination of the arrhythmia. This delay in the initiation of the confirmation period is useful when the arrhythmia is of a type that will not terminate immediately following the ATP therapy delivery. According to another aspect of the invention, confirmation is generally performed up until the time of shock delivery so that shock delivery may be aborted if the arrhythmia terminates just prior to the scheduled time of shock.

In one embodiment, the system also performs synchronization so that any delivery of a high-voltage shock is synchronized to the cardiac rhythm of the heart. Synchronization is performed during at least a portion of the confirmation period.

According to another aspect of the current invention, a method of treating an arrhythmia of the heart is provided. The method includes detecting the arrhythmia, controlling delivery of anti-tachy pacing (ATP) pulses to the heart based on at least one programmable parameter, and controlling delivery of a high-voltage shock to the heart based on the at least one programmable parameter in a manner that ensures that a time of delivery of the high-voltage shock is unaffected by the delivery of the ATP pulses. The method may include controlling delivery of ATP pulses based on a programmed shock energy of the high-voltage shock.

Other scopes and aspects of the current invention will be apparent from the following description and the accompanying drawings.

DETAILED DESCRIPTION OF THE DRAWINGS

Figure 1:
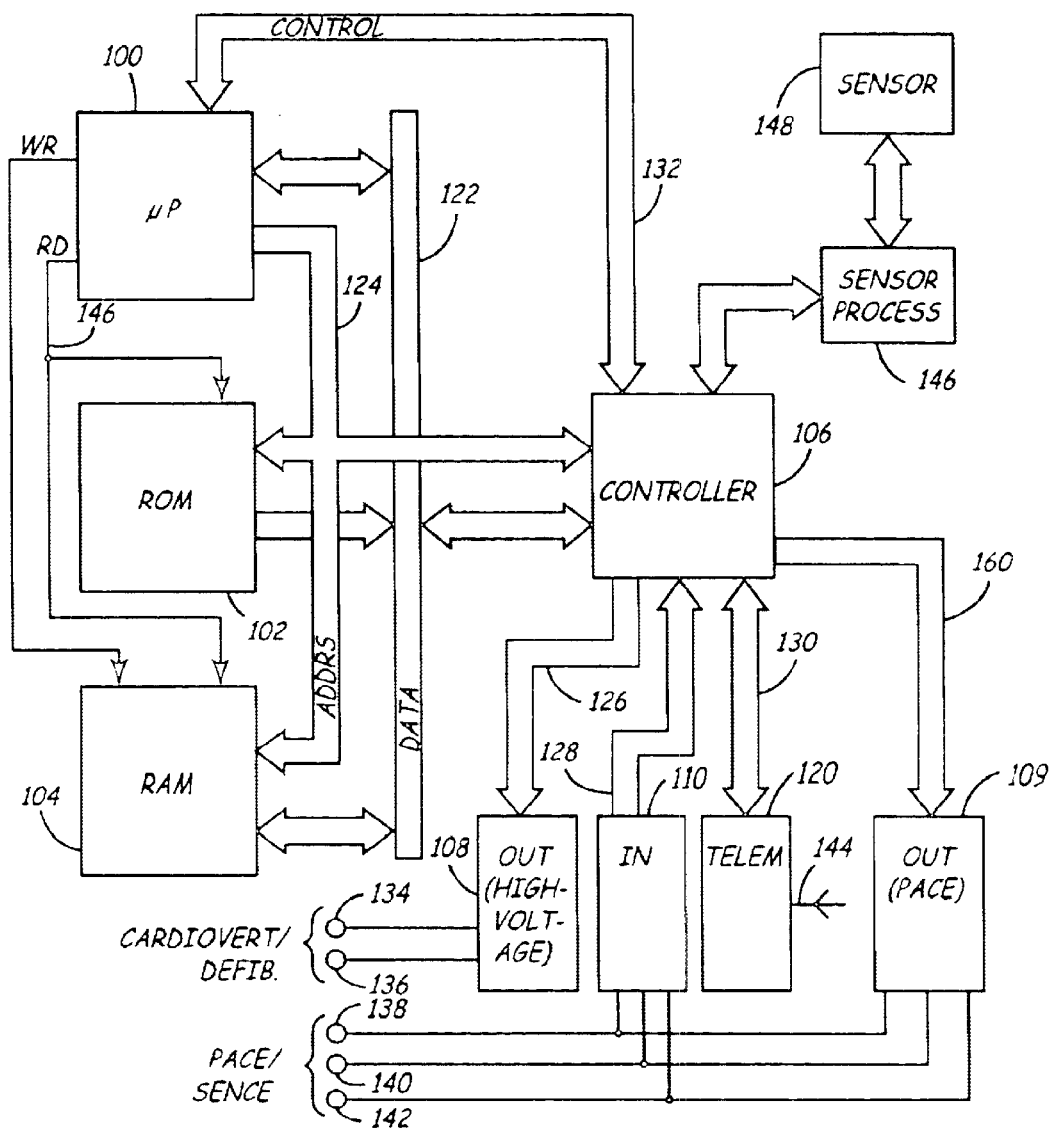
FIG. 1 is a block functional diagram of an illustrative embodiment of a cardioverter/pacemaker according to the present invention.

FIG. 1 is a block functional diagram of an illustrative embodiment of a pacemaker cardioverter/defibrillator (ICD) that may be employed according to the present invention. As illustrated, the device is embodied as a microprocessor based stimulator. However, other digital and/or analog circuit embodiments are possible within the scope of the invention. For example, devices having general structures as illustrated in U.S. Pat. No. 5,251,624 issued to Bocek et al., U.S. Pat. No. 5,209,229 issued to Gilli, U.S. Pat. No. 4,407,288, issued to Langer et al, U.S. Pat. No. 6,662,688. issued to Haefner et al., U.S. Pat. No. 5,885,593 issued to Olson et al., U.S. Pat. No. 4,821,723, issued to Baker et al. or U.S. Pat. No. 4,967,747, issued to Carroll et al., all incorporated herein by reference in their entireties, may also be usefully employed in conjunction with the present invention. Similarly, while the device of FIG. 1 takes the form of a ventricular pacemaker/cardioverter, the present invention may also be usefully employed in a device having atrial pacing and cardioversion capabilities. Therefore, FIG. 1 should be considered illustrative, rather than limiting with regard to the scope of the invention.

The primary elements of the apparatus illustrated in FIG. 1 are a microprocessor 100, read-only memory (ROM) 102, random-access memory (RAM) 104, a digital controller 106, an input amplifier circuit 110, two output circuits 108 and 109, and a telemetry/programming unit 120. Read-only memory may store the basic programmed instructions to be executed by microprocessor 100, and may further store parameters to define the various timing intervals employed by the cardioverter. RAM 104 generally stores data and variable control parameters, such as programmed pacing rate, programmed cardioversion intervals, pulse widths, pulse amplitudes, and so forth that may be programmed into the device by the physician. Random-access memory 104 also stores derived values, such as the stored time intervals separating tachyarrhythmia pulses and the corresponding high-rate pacing interval.

Controller 106 performs all of the basic control and timing functions of the device. Controller 106 includes at least one programmable timing counter, which is initiated upon detection of a ventricular contraction, and which times intervals thereafter. This counter is used to generate the basic timing intervals used to deliver anti-tachy pacing (ATP) pulses, and to measure other intervals used within the context of the current invention. On time-out of the pacing escape interval or in response to a determination that a cardioversion or defibrillation pulse is to be delivered, controller 106 triggers charging of output circuit 108 so that the appropriate shock waveform may be delivered, as discussed below.

Following generation of stimulus pulses, controller 106 may be utilized to generate corresponding interrupts on control bus 132, causing microprocessor 100 to perform any required mathematical calculations and other operations associated with selection of anti-tachyarrhythmia therapies according to the present invention. A timing/counter circuit in controller 106 also may also control timing intervals such as ventricular refractory periods, as is known in the art based on parameters stored in RAM 104 of ROM 102.

Controller 106 may also generate interrupts to microprocessor 100 on the occurrence of sensed ventricular beats. In addition, controller 106 may provide a timer value on data bus 122 to be used by microprocessor 100 in determining whether a tachyarrhythmia is present. This circuit may also be used to measure cardiac cycle lengths within the context of the current invention.

Output stage 108 contains a high-output pulse generator capable of generating cardioversion pulses of at least 0.1 joules, to be applied to the patient's heart. Typically the high output pulse generator includes one or more high-voltage capacitors, a charging circuit, and a set of switches to allow delivery of monophasic or biphasic cardioversion or defibrillation pulses via electrodes 134 and 136. The electrodes typically are large surface area electrodes mounted subcutaneously, or on or in the heart. Other electrode configurations may also be used, including two or more electrodes arranged within and around the heart.

In addition to output circuit 108, output circuit 109 is provided to generate pacing pulses. This circuit contains a pacing pulse generator circuit that is coupled to electrodes 138, 140 and 142, and which are employed to accomplish cardiac pacing, including ATP pacing pulses, by delivery of a electrical stimulation between electrode 138 and one of electrodes 140 and 142. Electrode 138 is typically located on the distal end of an endocardial lead, and is typically placed in the apex of the right ventricle. Electrode 142 may be a ring or coil electrode located on an endocardial lead slightly proximal to the tip electrode 138, or may be another electrode positioned inside or outside the heart. Output circuit 108 may be controlled by controller 106 via control bus 126. Controller 106 may determine the time, amplitude and pulse width of the pulses to be delivered, and may also determine which electrode pair will be employed to deliver the pulses.

Input amplifier 110 receives cardiac signals on a selected pair of electrodes 138 and 142. Signals indicating both the occurrence of intrinsic and paced ventricular beats are provided to the controller 106 via bus 128. In one embodiment, controller 106 provides an interrupt to microprocessor 100 via control bus 132 following a detected beat, allowing the microprocessor to perform any necessary calculations or to update values stored in RAM 104.

In one embodiment, one or more physiologic sensors 148 are included in the system. For example, sensor(s) 148 may include a hemodynamic sensor such as an impedance sensor as disclosed in U.S. Pat. No. 4,865,036, issued to Chirife, or a pressure sensor as disclosed in U.S. Pat. No. 5,330,505, issued to Cohen, both of which are incorporated herein by reference in their entireties. Alternatively, sensor 148 may be a demand sensor for measuring cardiac output parameters, such as an oxygen saturation sensor disclosed in U.S. Pat. No. 5,176,137, issued to Erickson et al. or a physical activity sensor as disclosed in U.S. Pat. No. 4,428,378, issued to Anderson et al., both of which are incorporated herein by reference in their entireties. Sensor processing circuitry 146 transforms the sensor output into digitized values for use in conjunction with detection and treatment of arrhythmias.

External control of the implanted cardioverter/defibrillator is accomplished via telemetry/control block 120 that controls communication between the implanted cardioverter/pacemaker and an external programmer. Any conventional programming/telemetry circuitry is believed workable in the context of the present invention. Information entering the cardioverter/pacemaker from the programmer is passed to controller 106 via bus 130. Similarly, information from the cardioverter/pacemaker is provided to the telemetry block 120 via bus 130.

Figure 2:
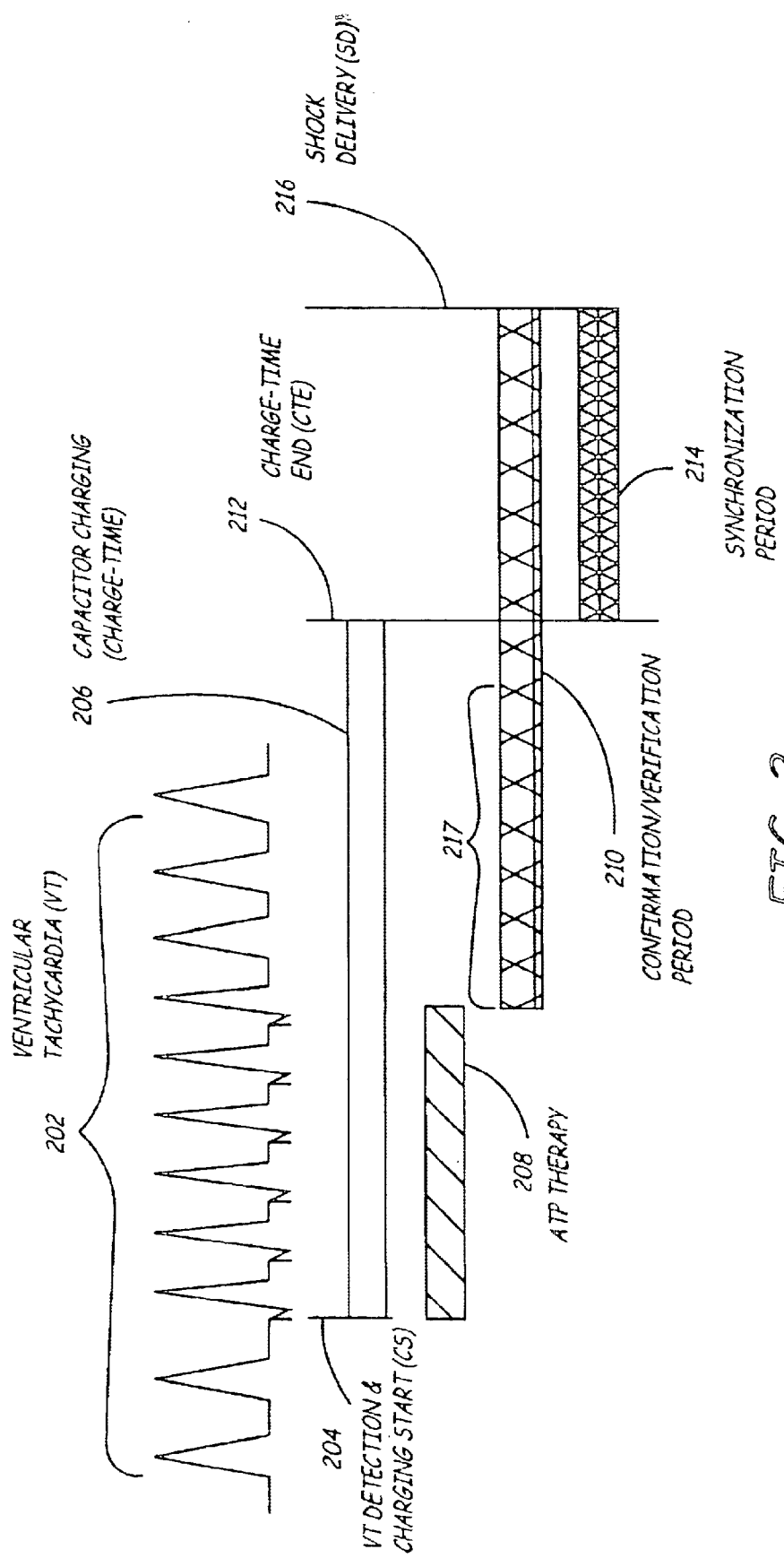
FIG. 2 is a timing diagram illustrating ventricular tachycardia that is being treated by anti-tachy pacing according to one embodiment of the present invention.

FIG. 2 is a timing diagram illustrating a ventricular arrhythmia (VA) event that is being treated by anti-tachy pacing (ATP) according to the present invention. As illustrated in FIG. 2, a VA rhythm 202 starts and continues for an unspecified duration. A device such as the exemplary ICD discussed above in reference to FIG. 1 detects the VA at detection time 204. VA detection at detection time 204 starts charging of a high-power capacitor, which continues during a charging time period 206. Delivery of one sequence of ATP therapy may be initiated substantially at time 204 or sometime thereafter, and continue during an ATP therapy time period 208.

After completion of ATP therapy, a confirmation/verification time period 210 begins. During this confirmation/verification period 210, the ICD device determines whether ATP therapy was successful in returning the patient to a normal sinus rhythm. This determination may be made based on detecting a ventricular rate below the programmed pre-determined rate, and/or by using additional waveform morphology criteria. The confirmation/verification process corresponding to time period 210 may be performed on a beat-by-beat basis, and generally is terminated when the arrhythmia termination is detected or sometime thereafter. If the arrhythmia does not terminate, period 210 may culminate in shock delivery (SD) at a shock delivery time 216.

FIG. 2 further illustrates that capacitor charging is completed at charge-time end (CTE) 212. At CTE 212 or sometime thereafter, a synchronization period 214 begins only if the VA is still detected as being present. The purpose of synchronization period 214 is to evaluate the periodicity of the VA events so as to ensure that the shock delivery at shock delivery time 216 is synchronized to an R-wave of the cardiac cycle. In this embodiment, the synchronization period 214 occurs simultaneously with a portion of confirmation/verification period 210. This allows termination of the VA to be detected up to the actual time of the shock delivery. If VA termination is detected, delivery of the shock is aborted.

In the embodiment shown in FIG. 2, shock delivery at time 216 occurs after synchronization period 214 is completed. It is important to note that delivery of ATP therapy during time 208 does not increase the time required to deliver this shock. That is, shock delivery occurs at substantially the same time as it would have occurred without the administration of the ATP therapy. Additionally, because the system determines whether the VA terminated during time period 210, which extends substantially to shock delivery at time 216, shock delivery may be aborted even if VA termination occurred just prior to time 216. This is particularly important where "type 2 breaks" are involved, since this type of rhythm transitions to normal sinus rhythm more gradually. This will be discussed in more detail below.

As discussed above, the current invention provides delivery of ATP therapy without extending the time-to-shock. To ensure that this is the case, the system imposes several limitations regarding the delivery of ATP therapy. First, according to one embodiment of the invention, ATP therapy delivery is limited to a predetermined number of sequences. This predetermined number may be limited to only a single sequence to reduce the time required to complete this therapy. Second, ATP therapy is only delivered if the time period 206 for charging the high-voltage capacitor is long enough to make the ATP delivery "transparent". Since this charge time is directly related to the amount of charge to be transferred to the high-voltage capacitors, this second requirement may be stated in terms of the programmed energy of the shock, which must be greater than a predetermined minimum shock value. Finally, ATP therapy will only be delivered when the cycle length of the detected arrhythmia at the time of the initial detection is less than a programmed maximum ventricular cycle length so that the entire ATP sequence may be delivered before completion of the capacitor charging. This requirement ensures that a complete sequence of ATP therapy can be delivered while not extending the time to shock delivery if the VA is not terminated. The foregoing requirements assume that other parameters relevant to ATP therapy, including the number of ATP pulses and the ATP pulse intervals, are either fixed or may be set to a limited number of values during ICD programming.

The above discussion regarding timing requirements can be summarized by the following equation:

$$\text{Charge\_Time} \geq \text{ATP\_Time} + \text{Confirm\_Time\_Post\_ATP}.$$

That is, the charge time ("Charge_Time") required to charge the capacitors, shown in FIG. 2 as time period 206, must be greater than or equal to the time period 208 required to deliver the ATP therapy ("ATP_Time") plus that portion 217 of the confirmation time period 210 that is needed to determine if the ATP therapy terminated the arrhythmia ("Confirm_Time_Post_ATP"). If this criterion is satisfied, shock delivery can occur without being impacted by the ATP. For example, if the ATP_Time 208 is 3 seconds and the Confirm_Time_Post_ATP is 4 seconds, then Charge_Time must be $\geq 7$ seconds in order to ensure that ATP therapy does not impact shock delivery. Given these constraints, and assuming that 7 seconds is required to charge the capacitors to 30 joules, the MinShock value must be selected to be at least 30 joules. Alternatively, with a predetermined charge time of 7 seconds, a physician is limited to programming ATP parameters such that the cumulative time required for ATP_Time+Confirm_Time_Post_ATP to no more than 7 seconds.

In an alternative embodiment of the invention, the ICD automatically adjusts the ATP_Time and Confirm_Time_Post_ATP based on a predetermined Charge_Time. As battery resources are used, the Charge_Time increases for any programmed shock value. The device, in turn, will automatically increase the ATP_Time and/or Confirm_Time_Post_ATP to make better use of the Charge_Time. This may be accomplished, for example, by changing one or more ATP therapy parameters, such as the number of pacing pulses in the ATP sequence or the pulse interval length.

Figure 3:
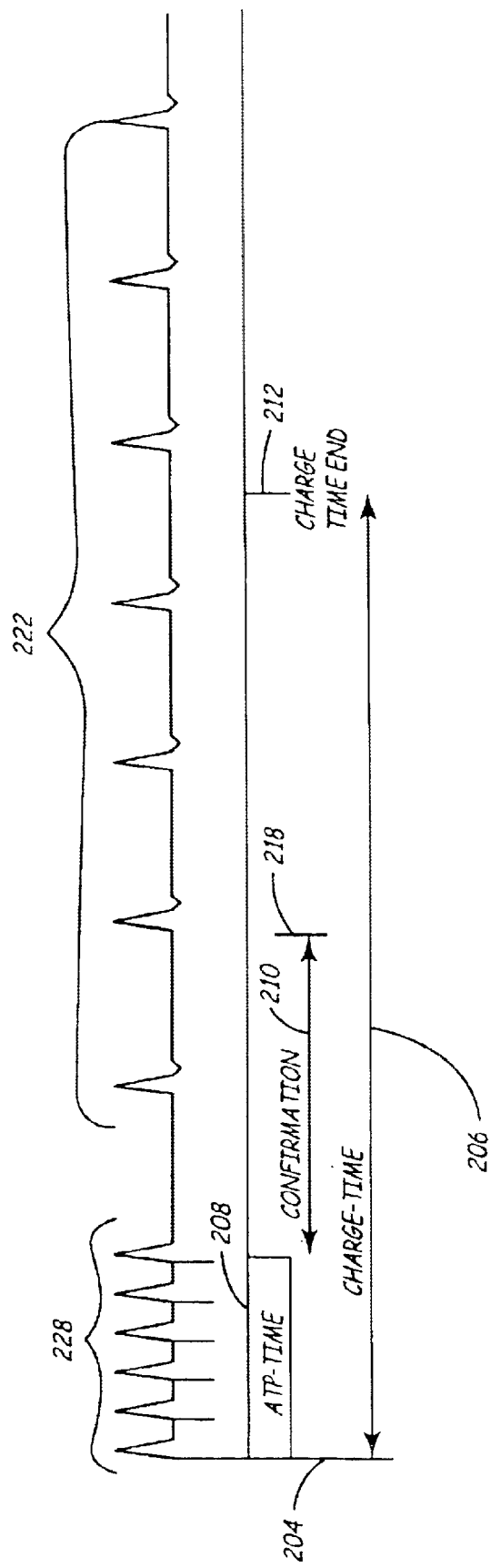
FIG. 3 is a timing diagram illustrating successful ATP therapy delivery.

FIG. 3 is a timing diagram illustrating successful ATP therapy delivery using one embodiment of the present invention. In FIG. 3, time periods that are similar to those shown in FIG. 2 are labeled with like numeral designations. According to the embodiment of FIG. 3, a sequence of ATP pulses 228 is delivered during time 208. As with any of the embodiments of the invention discussed herein, this sequence might consist of burst, ramp, or ramp-plus-pacing pulses, among others. Confirmation/verification period 210 begins at the end of ATP therapy delivery and ends upon detection of VA termination at time 218 where a transition to a normal sinus rhythm 222 occurs. Charging of capacitors ends either upon VA termination at time 218 or, as shown here, at charge-time end (CTE) 212, at which time shock delivery is aborted and the accumulated charge can be left on the capacitors or can be drained or dumped.

FIG. 3 illustrates the manner in which the above criterion is satisfied such that the Charge_Time 206 is equal to, or greater than, ATP_Time 208 plus the confirmation time 210. It may be noted that in this case, confirmation time 210 corresponds to the Confirm_Time_Post_ATP 217 of FIG. 2. Charge_Time 206 may be selected by a physician at device implant, and must be associated with a shock energy at least equal to, or greater than, a minimum shock value "Minshock" if ATP is to be delivered. The Minshock parameter may be a system parameter programmed during device manufacture.

Figure 4:
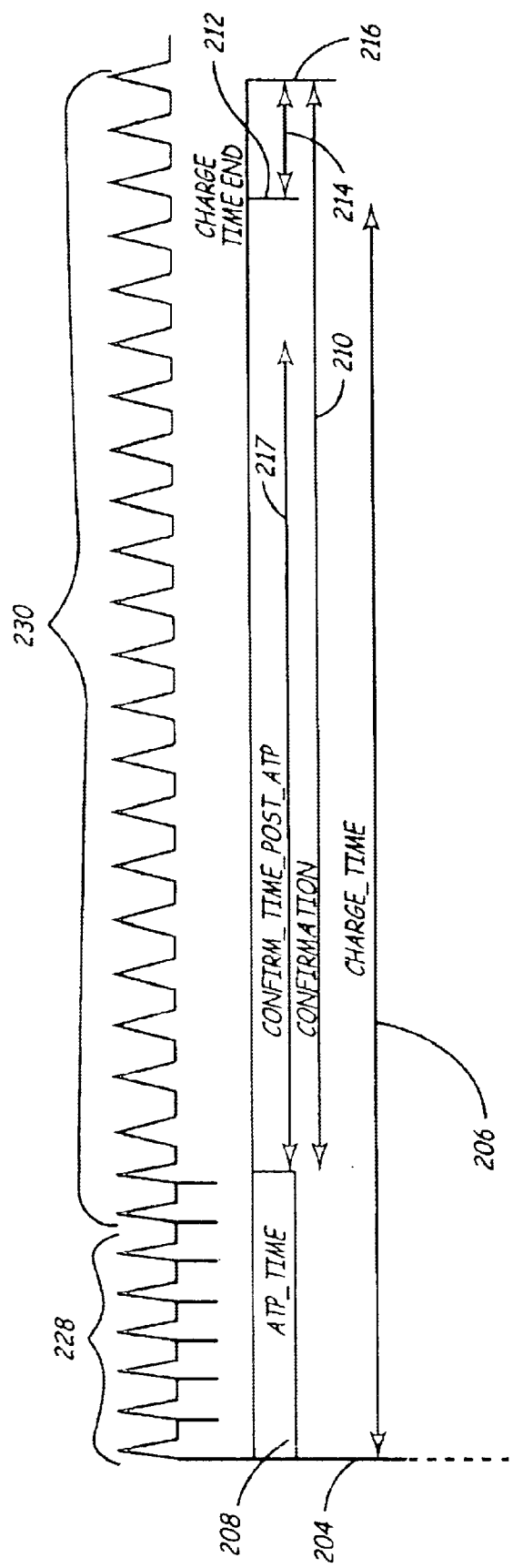
FIG. 4 is a timing diagram illustrating unsuccessful ATP therapy according to one embodiment of the present invention.

FIG. 4 is a timing diagram illustrating unsuccessful ATP therapy according to one embodiment of the present invention. As in FIG. 3, a sequence of ATP therapy 228 is delivered during time 208. Unlike FIG. 3, ATP therapy fails to terminate the VA and the episode continues during time 230. Confirmation period 210 begins at the end of ATP therapy or sometime thereafter, and continues past charge end at time 212 until sometime before, or at, the time of shock delivery 216. The synchronization period 214 begins following charge-time end 212, and culminates with shock delivery at time 216. If the VA terminates during synchronization period 214 (not shown in this example), shock delivery is aborted and the accumulated charge on the capacitors would be retained for subsequent use, drained or dumped.

As in the foregoing example, ATP therapy is enabled only if the shock is set above the MinShock value so that the Charge_Time 206 is equal to, or greater than, the ATP_Time 208 plus the Confirm_Time_Post_ATP. The times assigned to these periods may correspond to those discussed above in reference to FIG. 2 with 30 joules selected as the programmed value.

Turning now to a discussion on various ways VA rhythms are terminated, it has been determined that VA terminations may be categorized using at least two identifications. "Type 1 breaks" occur almost immediately after the last pacing pulse of an ATP therapy sequence is delivered, as depicted in FIG. 3. In contrast, "type 2 breaks" involve several VA depolarizations occurring after delivery of the ATP therapy sequence has concluded. Thus, to detect a type 2 break, the ICD of one embodiment of the current invention is capable of detecting the return to normal sinus rhythm up to the point of shock delivery at time 216 so that unneeded shock delivery is prevented in most cases. This requires continued detection throughout synchronization period 214.

Figure 5:
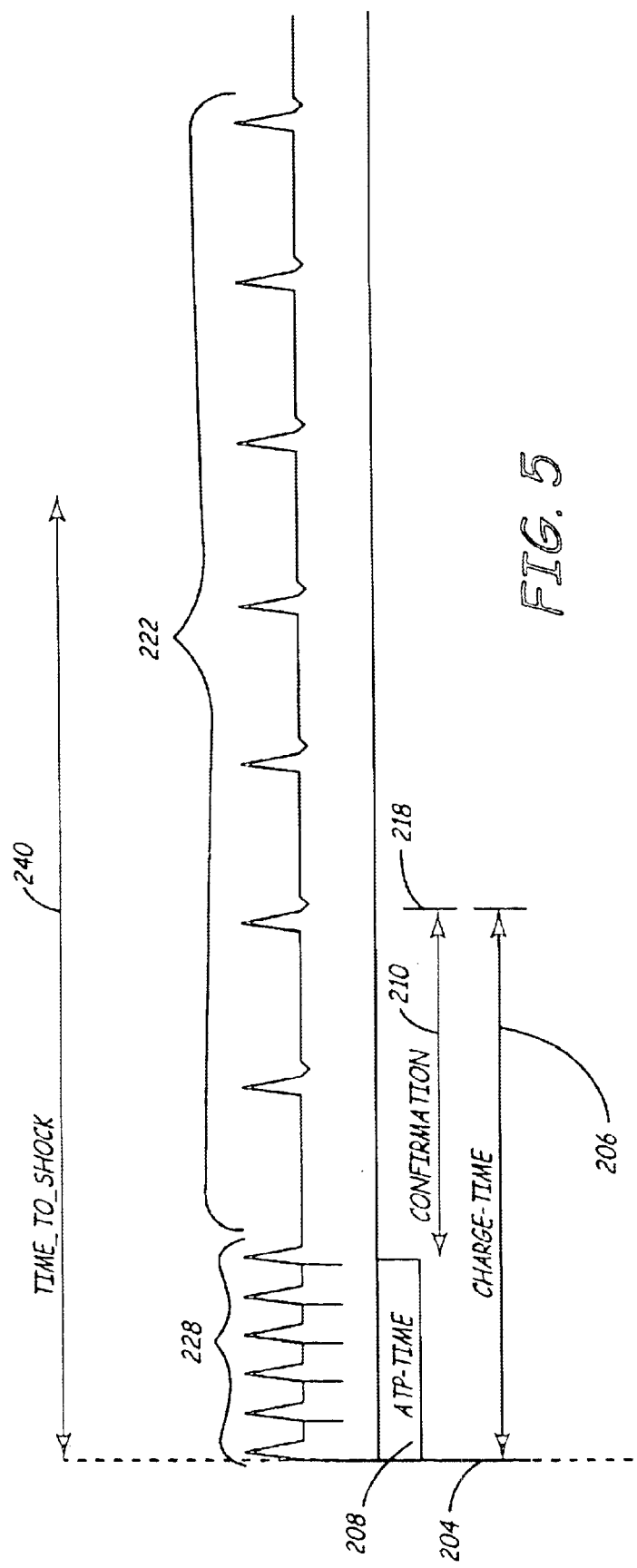
FIG. 5 is a timing diagram illustrating successful termination of a VA utilizing an alternative embodiment of the invention.

FIG. 5 is a timing diagram illustrating a successful termination of a VA due to ATP therapy using an alternative embodiment of the present invention. As occurs in FIG. 3, one sequence of ATP therapy 228 is delivered. Therapy occurs in a manner that is similar to that shown in FIG. 3.

That is, the confirmation period 210 begins at the end of ATP therapy delivery and ends upon detection of VA termination at time 218 just after the time where a transition to a normal sinus rhythm 222 occurs. It may be noted that in this case, confirmation time 210 corresponds to the Confirm_Time_Post_ATP 217 of FIG. 2. In this embodiment, charging of capacitors during Charge_Time 206 is shown to end at time 218 when VA termination is detected in order to conserve battery resources.

In the embodiment of FIG. 5, Charge_Time 206 is not the specified parameter that controls ATP therapy delivery. Instead, a programmable "time-to-shock" period 240 is defined to control the timing of the shock delivery. The time-to-shock period 240, rather than Charge_Time 206, effectively determines the maximum time available for use in charging the capacitors, since charge end must occur prior to the start of synchronization. The charge-end time, in turn, defines the time available for ATP_Time and Confirm_Time_Post_ATP in the manner discussed above. It may be noted that charge end may occur sometime prior to the expiration of the time-to-shock period, if desired.

In this way, according to the present invention, the time-to-shock period 240 may be selected in place of Charge_Time 206 to control system timing at the election of a physician. This may be desirable if the physician does not wish to select a high-energy shock value. For example, a physician may wish to program a 10-joule shock. Since that relatively low-energy shock value results in a shorter capacitor charge time, the physician may instead choose the time-to-shock interval to control the ATP therapy and shock delivery. The length of this time period is selected based on what is considered a safe delay between the on-set of the VA and the shock delivery. Therefore, if approximately three seconds are required to charge an output capacitor to 10 joules, but seven seconds are required prior to synchronization to allow for ATP therapy delivery and subsequent confirmation (to allow for the potential for type-2 breaks), the physician will program the time-to-shock period to at least seven seconds. This embodiment therefore allows the physicians to select a low-power shock while maintaining adequate time to detect VA termination. In this alternative embodiment, the governing timing relationship is as follows:

$$Time\_to\_Shock \geq ATP\_Time + Confirm\_Time\_Post\_ATP$$

That is, the Time_to_Shock must be greater than the sum of ATP_Time and the parameter Confirm_Time_Post_ATP, wherein the latter parameter is the amount of time allowed for confirmation following ATP therapy delivery and prior to the start of synchronization. This parameter may be selected in any of the ways discussed below in regards to selection of Confirm_Time_Post_ATP.

In yet another embodiment of the invention, the Time_to_Shock period discussed above is automatically adjusted by the system rather than being pre-selected by a user. This parameter adjustment occurs as the battery ages, requiring more time to charge the capacitors to a predetermined energy level. For example, the Time_to_Shock parameter may be selected to be substantially the same as the capacitor charge time. In this embodiment, battery impedance changes and/or capacitor formation calculations may be used to detect battery aging. This determination may then result in the automatic re-selection of a different ATP therapy that requires a longer delivery time, such as additional ATP sequences or an ATP sequence having a longer cycle time. This is allowed because of the longer capacitor charge time caused by battery aging. In yet another embodiment of the invention, the Time_to_Shock parameter may be implemented by counting a programmable number of beats to define a time period rather than by using a selectable timeout.

Figure 6:
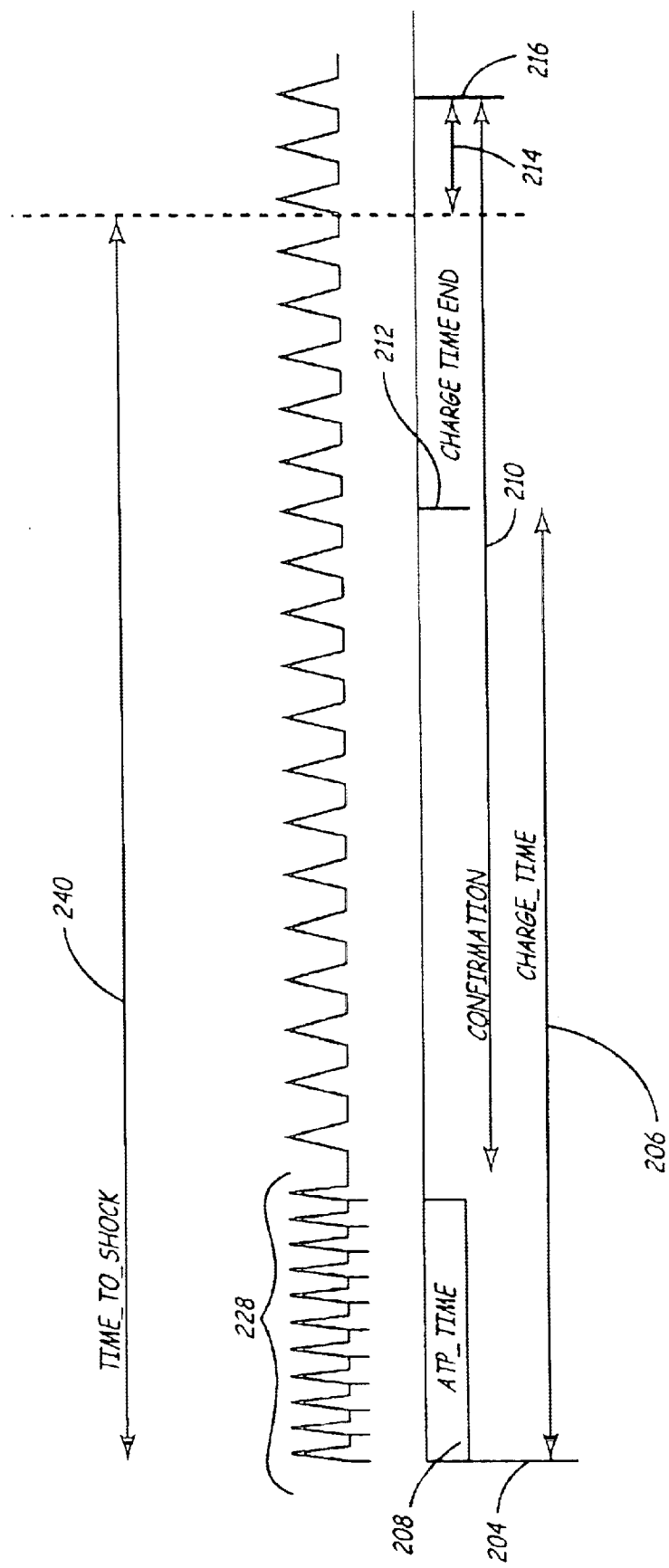
FIG. 6 is a timing diagram illustrating an unsuccessful treatment of a VA due to ATP therapy when the time-to-shock parameter is programmed.

FIG. 6 is a timing diagram illustrating an unsuccessful termination of a VA due to ATP therapy when the Time_to_Shock parameter is used. This diagram may apply to a Time_to_Shock parameter that is pre-programmed by a user, as well as a parameter that is automatically adjusted by the system as discussed above. FIG. 6 is similar to FIG. 5, with a sequence of ATP therapy 228 being delivered after the VA is detected. Confirmation period 210 begins at the end of ATP therapy and ends substantially at the same time as synchronization period 214 concludes. Capacitor charging occurs during period 206, ending at charge end time 212. Assuming a predetermined synchronization time period 214 is utilized, the length of the Time_to_Shock period 240 determines the time 216 at which shock will be delivered if the VA is not terminated, as is the case illustrated in FIG. 6. If the VA had slowed or been terminated during confirmation period 210 or synchronization period 214, shock delivery would have been aborted and the accumulated charge on the capacitors retained for subsequent use, drained or dumped.

As discussed above, this time-to-shock period defines a maximum allowable capacitor charge time, since charge end must occur prior to initiation of the synchronization period 214. However, the charge time may be somewhat less than the time-to-shock period, as illustrated in FIG. 6. Defining a longer time-to-shock period allows a longer confirmation period 210, which is particularly beneficial in detecting type 2 breaks, as discussed above.

Figure 7:
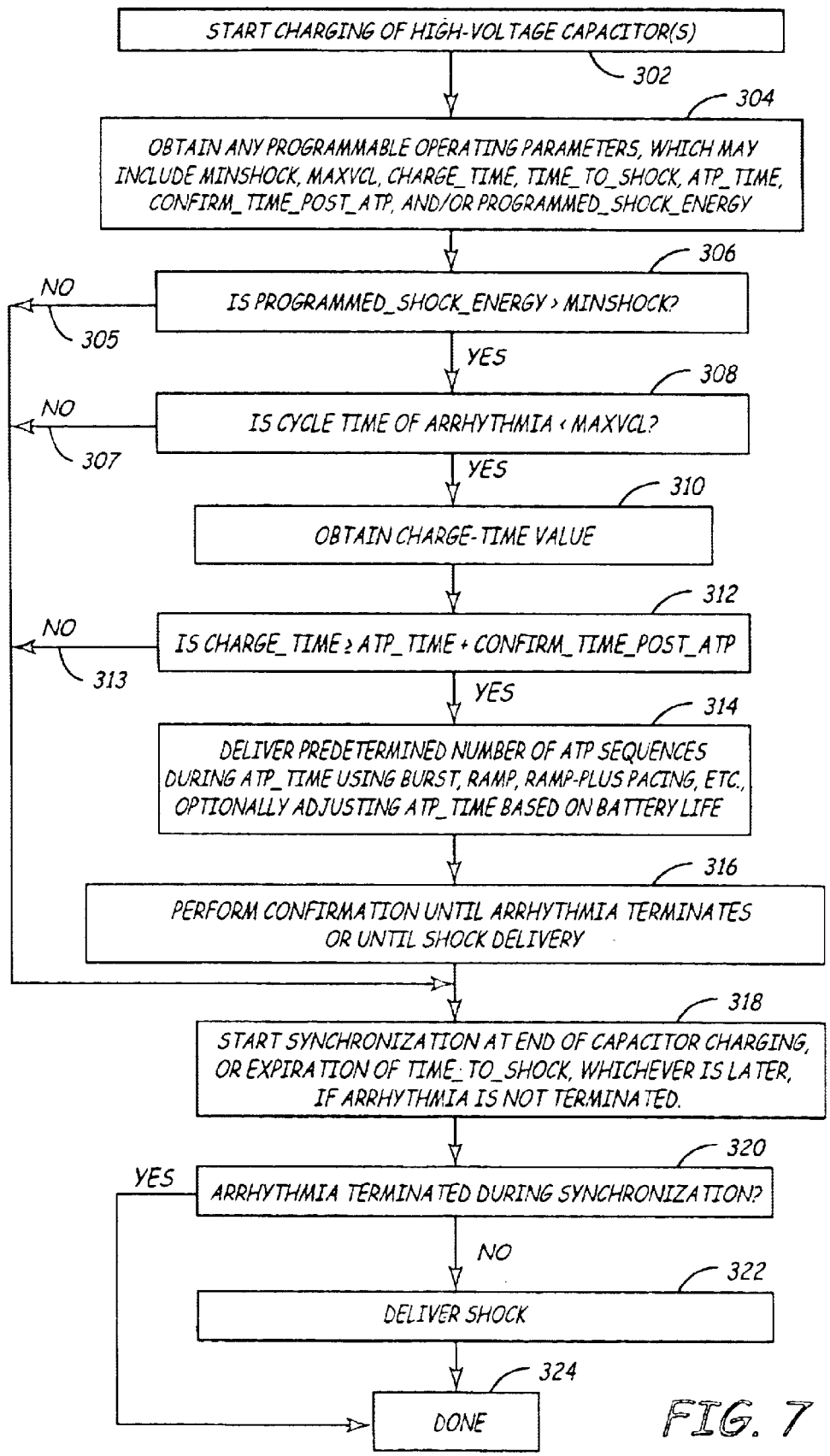
FIG. 7 is a flowchart illustrating one embodiment of the current invention.

FIG. 7 is a flowchart illustrating execution of a method of operating an implantable device in accordance with an embodiment of the present invention. First, an arrhythmia is detected (300). The detection may use rate and/or waveform morphology analysis of a signal sensed by input circuit 110 (FIG. 1). Such analysis may be performed by microprocessor 100. During detection, various attributes of the arrhythmia, including the cardiac cycle length, are stored in memory such as RAM 104.

After the arrhythmia is detected, charging of one or more high-voltage capacitors may be initiated (302). These high-voltage capacitors may be included in high-voltage output circuit 108 (FIG. 1), as discussed above. Next, any programmable and/or predetermined operating parameters may be obtained (304). Such parameters may be stored in RAM 104 and/or ROM 102. Such parameters may include the minimum shock energy ("Minshock"), the maximum ventricular cycle ("Maxvcl"), the high-voltage capacitor charging time ("Charge_Time"), the time from arrhythmia detection to the start of cardiac synchronization ("Time_to_Shock"), the time allowed for ATP therapy ("ATP_Time"), the time allowed for confirmation following ATP delivery and prior to charge end ("Confirm_Time_Post_ATP"), and/or the programmed shock energy ("Programmed_Shock_Energy"), all of which will be described further below.

In some instances, some of the above-described parameters may be predetermined values that are not programmable. For example, Minshock and Maxvcl may be loaded into ROM 102 at the time of device manufacture. Other parameters may be associated with minimum predefined values. For example, ATP_Time and Confirm_Time_Post_ATP could be associated with predetermined minimum values that are selected based on the minimum time period ATP therapy delivery and post ATP confirmation can be usefully performed. Other parameters may be selected by a physician prior to device implant. Selection of the various parameters will be discussed further below.

After predetermined and/or programmable operating parameters are obtained, these parameters may be used in accordance with the invention to determine whether ATP therapy may be delivered. First, it may be determined whether Programmed_Shock_Energy is greater than Minshock (306). As discussed above, the Programmed_Shock_Energy parameter indicates the programmed energy level (e.g., 30 Joules) for delivery of a high-voltage shock. Generally, this parameter is selected by the implanting physician. This programmed energy level should be greater than the system value Minshock, which is the minimum shock energy that may be selected for shock delivery if ATP therapy is also to be delivered. In general, Minshock will be a predetermined parameter selected at the time of device manufacture. If Programmed_Shock_Energy is less than Minshock, enough time will not be available during capacitor charging to deliver ATP therapy so that shock delivery time is unaffected. Therefore, no ATP therapy will be delivered, and execution continues at step 318 as indicated by arrow 305. Otherwise, processing continues to step 308.

Next, the measured ventricular cardiac cycle time of the arrhythmia may be compared to the parameter Maxvcl (308). Maxvcl is the maximum ventricular cycle that can be associated with an arrhythmia if ATP therapy is to be delivered. If the measured cycle time of the arrhythmia as measured by an implantable device is greater than Maxvcl, ATP therapy cannot be used. This is because the long cycle time extends the time required to deliver a sequence of ATP therapy in a manner that will affect shock delivery time. Therefore, in this instance, processing continues at step 318, as indicated by arrow 307. Otherwise, if the measured cycle time is less than Maxvcl, processing continues to step 310. Maxvcl is generally a system parameter selected at the time of device manufacture.

In the next step, the parameter Charge_Time may be determined (310). This parameter is the time required to fully charge the high-voltage capacitor(s) of the device in preparation for shock delivery. This parameter will be determined based on the programmed shock energy "Programmed_Shock_Energy", the device circuitry, and the battery life. Methods for estimating capacitor charge time based on foregoing factors are known in the art.

After the value for "Charge_Time" have been obtained, it is determined whether "Charge_Time" is greater than, or equal to, the sum of "ATP_Time" and "Confirm_Time_Post_ATP" (312). As noted above, "ATP_Time" is the time for delivery of a predetermined number of sequences of ATP therapy. In one embodiment, the number of ATP sequences delivered is limited to "one" to minimize the time required to complete this therapy. In another embodiment, multiple ATP sequences may be delivered, although this may require selection of a larger programmed shock energy. "Confirm_Time_Post_ATP" is the minimum amount of time following completion of ATP therapy that is required to determine whether the ATP therapy terminated the arrhythmia.

ATP_Time and Confirm_Time_Post_ATP may be obtained in several ways based on the selected embodiment of the invention. In one embodiment, ATP_Time and Confirm_Time_Post_ATP could be associated with predetermined minimum system values that are provided at the time of device manufacture. These predefined minimum values are selected based on the minimum time needed to provide effective ATP therapy delivery and effectively perform post ATP confirmation, respectively. In another embodiment, a physician selects these values at time of implant based on therapy requirements. In yet another embodiment, the physician may optionally select these values, with the default values being used if no selection is made. In still another embodiment, these parameters are selected automatically by the system based on Charge_Time. These parameters may be adjusted based on battery life in the manner discussed above to optimally utilize the entire Charge_Time. That is, as the battery life increases, Charge_Time will increase, allowing more time for delivering ATP therapy and performing confirmation. This will be taken into consideration automatically by the system.

In any of the foregoing embodiments, if "Charge_Time" is less than the sum of "ATP_Time" and "Confirm_Time_Post_ATP", then ATP therapy is not provided, since the delivery of ATP therapy will adversely affect shock delivery time. In this case, processing continues to step 318, as shown by arrow 313. Otherwise, execution continues to step 314.

As discussed above, in still another embodiment of the invention, step 312 may be governed by an alternative relationship involving the Time_to_Shock parameter. In this instance, the relationship that dictates system operation is as follows:

$$\text{Time\_to\_Shock} \geq \text{ATP\_Time} + \text{Confirm\_Time\_Post\_ATP}$$

That is, the Time_to_Shock parameter must specify a time period that is greater than the sum of ATP_Time+Confirm_Time_Post_ATP, wherein the latter parameter is the amount of time allowed for confirmation following ATP therapy delivery.

Assuming the relationship of step 312 is met, ATP therapy is delivered (314). As noted above, a predetermined number of ATP sequences may be delivered. In a preferred embodiment, only a single ATP therapy sequence is delivered to minimize therapy delivery time. The ATP therapy may be delivered in burst, ramp, ramp-plus-pacing, or any of the other ATP therapy delivery modes known in the art.

Following ATP delivery, confirmation is performed until the arrhythmia is verified as having been terminated, or until the shock is delivered (316). This confirmation may be performed on a beat-by-beat basis. In this way, the shock delivery may be aborted up until the last minute if the arrhythmia breaks and normal sinus rhythm is resumed.

At the end of capacitor charging, or following Time_to_Shock, whichever is later, synchronization is initiated if the arrhythmia has not yet terminated (318). Synchronization is performed so that shock delivery occurs at a predetermined point in the cardiac cycle, which preferably is at the time of the R-wave. As noted above, the parameter Time_to_Shock, which specifies the time period between arrhythmia detection and the initiation of synchronization, may be used to delay the initiation of synchronization after the end of capacitor charging. This extends the time available for confirmation. Confirmation is also performed during synchronization so that a break in arrhythmia occurring during this time may be detected.

If the arrhythmia terminates during synchronization (320), shock delivery is aborted, and processing is complete (324.) Otherwise, shock delivery occurs when synchronization has been completed (322).

The inventive method of FIG. 7 allows ATP therapy to be delivered in conjunction with shock therapy without affecting the time of shock delivery. Those skilled in the art will recognize that variations of this method are possible within the scope of the current invention.

For example, the ordering of many of the steps illustrated in FIG. 7 are exemplary, and may be changed. In one embodiment, the ordering of steps 306 through 310 may be altered. In another embodiment, some of the steps may be omitted. As an example, one or more of steps 306 and 308 or 310 and 312 may be omitted, if desired. In yet another exemplary embodiment, confirmation may be limited to a time after capacitor charging is completed, as is described in the following paragraphs.

The foregoing embodiments describe use of confirmation prior to the completion of capacitor charging at charge end 212. In some instances, it is desirable to delay confirmation until after capacitor charging is completed. This is particularly true when the patient is prone to experiencing type 2 breaks. As discussed above, a type 2 break is a return to normal sinus rhythm some time following the termination of ATP therapy. In the case of a type 2 break, several ventricular depolarizations may occur following termination of the ATP therapy before the heart returns to a normal sinus rhythm. This is in contrast to a type 1 break that occurs almost immediately after the last pacing pulse of the ATP therapy is delivered. In these instances, it is desirable to delay the initiation of confirmation until after completion of capacitor charging, since performing confirmation prior to this time will not detect the break. This allows the confirmation to be completed more accurately and efficiently, particularly where type 2 breaks are involved.

Figure 8:
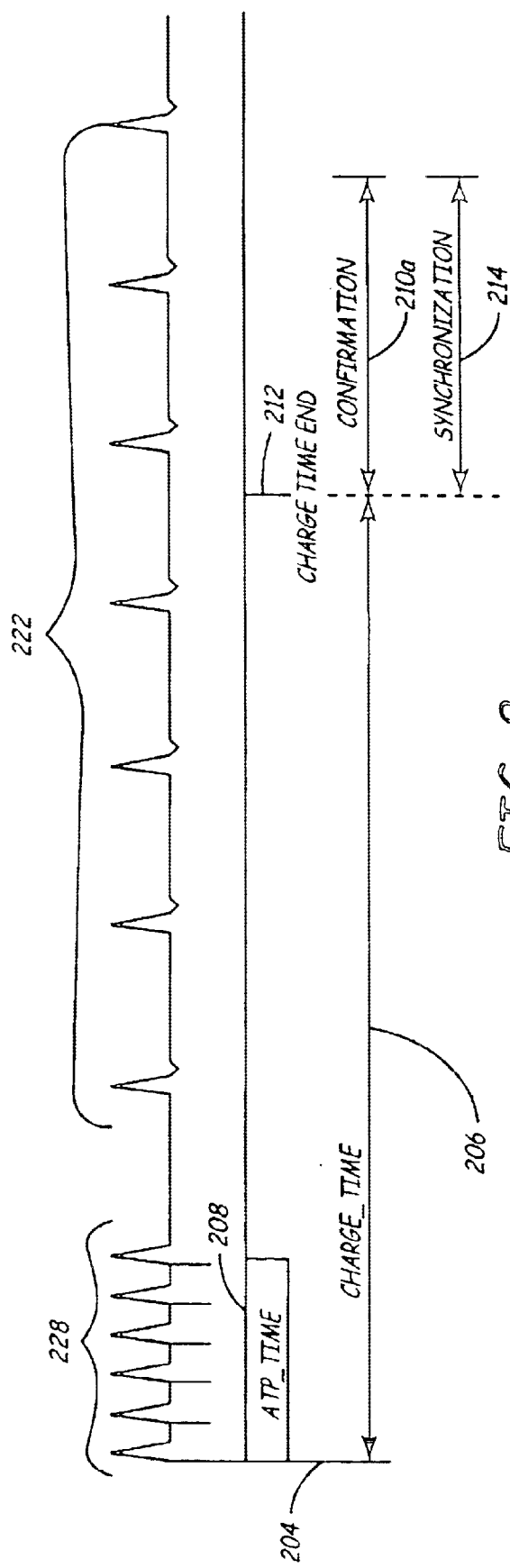
FIG. 8 is a timing diagram similar to that shown in FIG. 3, but illustrating confirmation that is initiated upon completion of capacitor charging.

FIG. 8 is a timing diagram similar to that shown in FIG. 3, but illustrating confirmation that is initiated upon expiration of Charge_Time. In this, and the following timing diagrams, time periods similar to those discussed above are labeled with like reference numerals. In FIG. 8, confirmation period 210a begins after Charge Time End 212, and may occur simultaneously with synchronization period 214. This embodiment allows synchronization to be completed upon a determination that shock delivery is needed. In another embodiment, synchronization 214 is initiated following completion of the confirmation period 210a, and only after it has been determined that the arrhythmia has not broken. This alternative may not be desirable, however, since shock delivery will be delayed.

Figure 9:
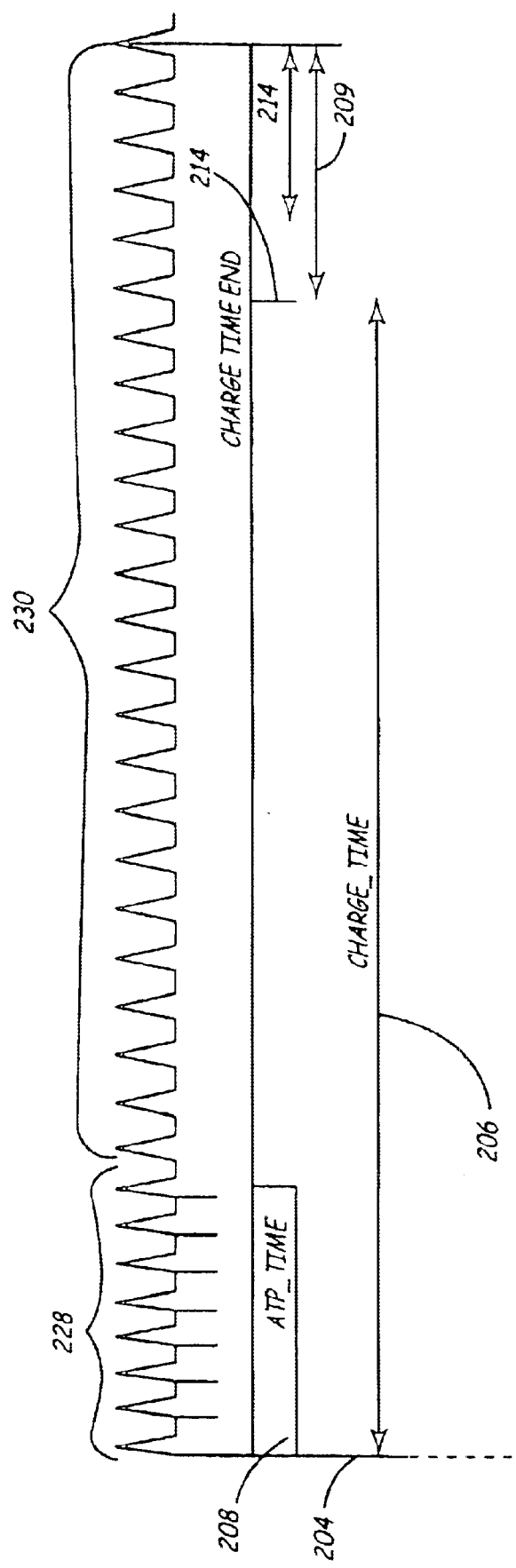
FIG. 9 is a timing diagram similar to that shown in FIG. 4, but illustrating the confirmation period being initiated upon completion of capacitor charging.

FIG. 9 is a timing diagram similar to that shown in FIG. 4, but illustrating confirmation period 210a initiated upon expiration of Charge_Time 206. In this embodiment, synchronization period 214 is initiated after confirmation period 210a has begun, providing additional time for confirmation to complete. As noted above, synchronization could alternatively be initiated after confirmation is completed.

Figure 10:
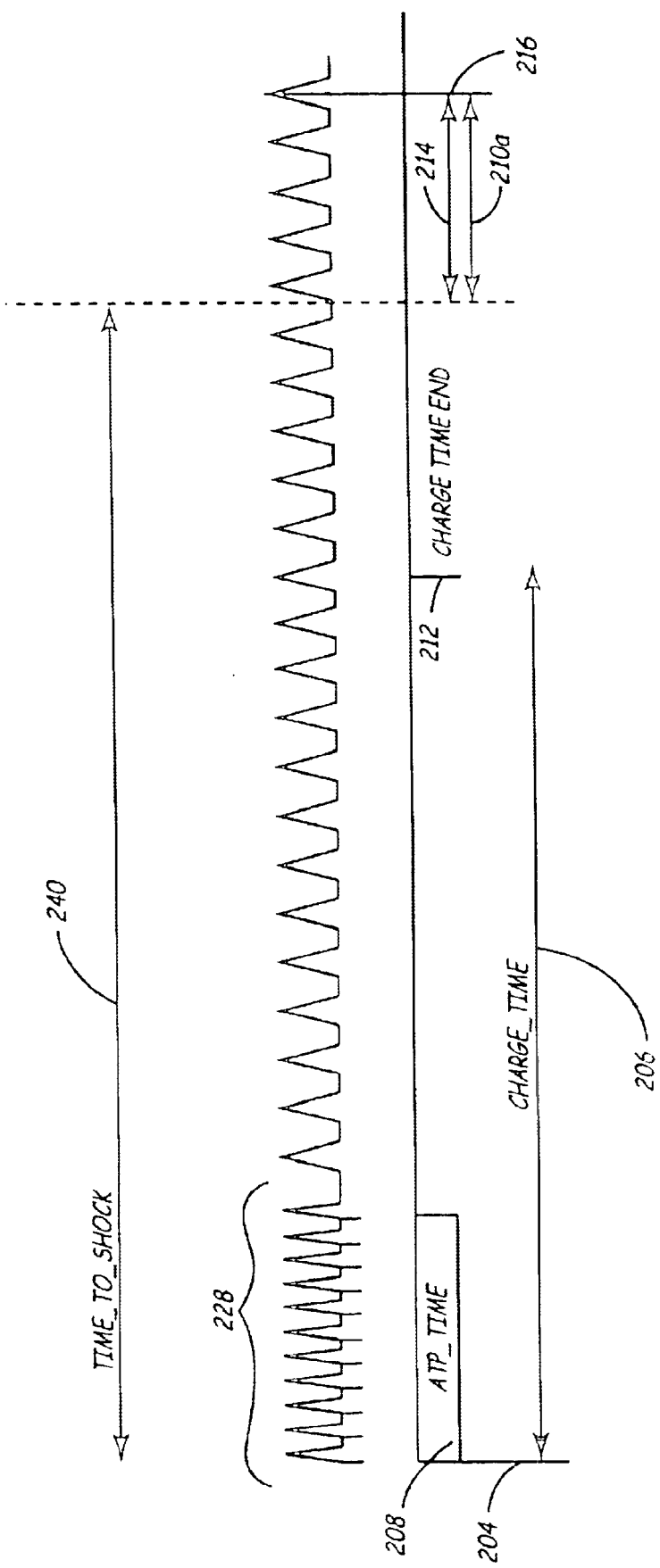
FIG. 10 is a timing diagram illustrating another embodiment wherein the confirmation period is initiated after capacitor charging is complete.

FIG. 10 is a timing diagram illustrating another embodiment wherein confirmation period 210a is initiated after capacitor charging is complete. In this embodiment, confirmation period 210a and synchronization period 214 are initiated after expiration of the programmable Time_to_Shock period 240 discussed above. Time_to_Shock may be programmed by an implanting physician, if desired, to provide additional time for a type 2 arrhythmia to terminate prior to the initiation of confirmation period 210a. If desired, expiration of the Time_to_Shock could initiate confirmation period 210a, with synchronization period 214 being initiated at some predetermined time thereafter, such as during or after confirmation period 210a It may be noted that the embodiment of FIG. 10 delays shock delivery, since confirmation period 210a is not initiated immediately following the completion of capacitor charging.

In a variation of the embodiment of FIG. 10, the Time_to_Shock period may be defined as a time period that commences upon expiration of ATP_Time rather than at detection of the arrhythmia. Expiration of Time_to_Shock period would initiate the confirmation period 210a in a manner similar to that discussed above.

As discussed above, the current invention provides availability of ATP therapy without extending the time-to-shock because of the ATP therapy. In regards to the embodiments shown in FIGS. 2 through 6, this was described using the following equations:

$$\text{Charge\_Time} \geq \text{ATP\_Time} + \text{Confirm\_Time\_Post\_ATP}$$

In the embodiments shown in FIGS. 8–10, confirmation does not start until after capacitor charging is complete, and Confirm_Time_Post_ATP is therefore zero. Therefore, in one embodiment wherein confirmation does not begin until after the completion of capacitor charging, the requirement is as follows:

$$\text{Charge\_Time} \geq \text{ATP\_Time}$$

As discussed above, ATP therapy may be limited to include only delivery of a predetermined number of sequences that can be completed prior to capacitor charge end. In one embodiment, only a single sequence is delivered to ensure the above relationship is met. Any type of ATP mode may be used, including burst, ramp, or any other mode.

In an alternative embodiment, a delay time "Delay_Time" may be defined to ensure that sufficient time will be provided for the arrhythmia to terminate following delivery of ATP therapy and prior to the completion of capacitor charging. In this embodiment, the requirement may be expressed as follows:

$$\text{Charge\_Time} \geq \text{ATP\_Time} + \text{Delay\_Time}$$

In these embodiments, if the predetermined relationship cannot be met based on the programmed shock energy, ATP therapy is not provided.

Figure 11:
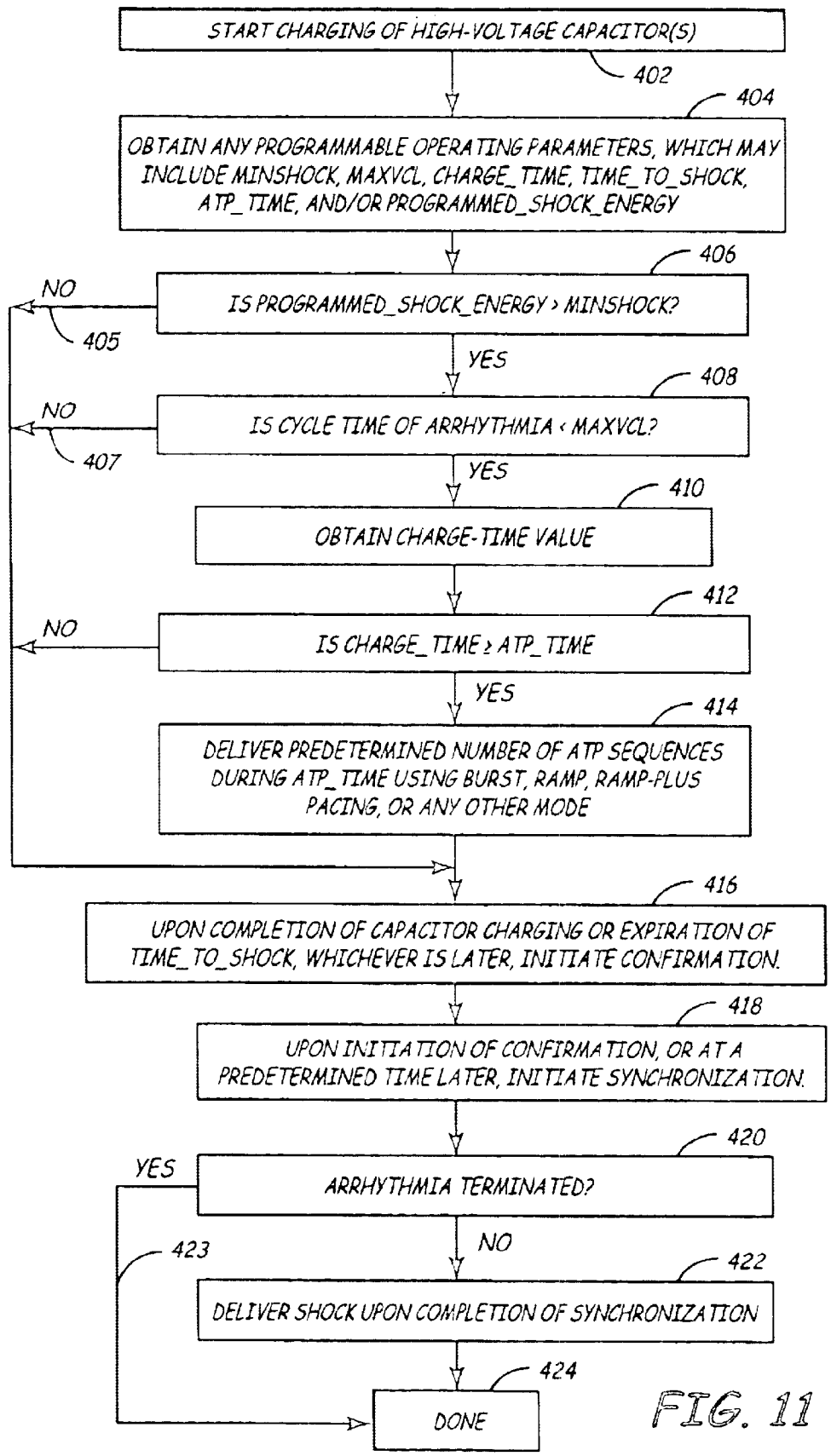
FIG. 11 is a flowchart illustrating execution of a method of operating an implantable device in accordance with an embodiment of the current invention wherein confirmation is initiated after capacitor charge end.

FIG. 11 is a flowchart illustrating execution of a method of operating an implantable device in accordance with an embodiment of the current invention wherein confirmation is initiated after capacitor charge end. First, an arrhythmia is detected as discussed above (400). Arrhythmia attributes include cardiac cycle length may optionally be stored in memory such as RAM 104.

After the arrhythmia is detected, charging of one or more high-voltage capacitors may be initiated (402). Next, any programmable and/or predetermined operating parameters may be obtained (404). Such parameters may include Minshock, Maxvcl, Charge_Time, Time_to_Shock, ATP_Time, Programmed_Shock_Energy, and/or the optional additional parameter Delay_Time discussed above. As discussed above, some of these parameters may be predetermined system values that are not programmable, whereas other parameters are programmable, and still others may be determined by the system based on battery life and other variable system conditions.

After predetermined and/or programmable operating parameters are obtained, these parameters may be used in accordance with the invention to determine whether ATP therapy may be delivered. In one embodiment, it may optionally be determined whether Programmed_Shock_Energy is greater than Minshock (406). If Programmed_Shock_Energy is less than Minshock, enough time will not be available during capacitor charging to deliver ATP therapy in a manner that does not affected shock delivery time. Therefore, no ATP therapy is available, and execution continues at step 416 as indicated by arrow 405. Otherwise, processing continues to step 408.

Next, the measured ventricular cardiac cycle time of the arrhythmia is optionally compared to the parameter Maxvcl (408) in a manner similar to that discussed above. If the measured cycle time of the arrhythmia is greater than Maxvcl, ATP therapy cannot be used, since use of the therapy will affect shock delivery time. Therefore, in this instance, processing continues at step 416, as indicated by arrow 407. Otherwise, if the measured cycle time is less than Maxvcl, processing continues to step 410.

In the next step, the parameter Charge_Time may be determined based on the programmed shock energy Programmed_Shock_Energy, the device circuitry, and the battery life as discussed above (410). This parameter is then used to determine whether ATP therapy may be delivered. If the value ATP_Time is greater than Charge_Time, then ATP therapy is not provided, since the delivery of ATP therapy will adversely affect shock delivery time. In a similar embodiment wherein a delay time "Delay_Time" is specified between the end of ATP delivery and the completion of capacitor charging, Charge_Time must be greater than the sum of ATP_Time and Delay_Time.

If the required relationship is not met, processing continues with step 416. Otherwise, ATP therapy may be delivered (414). As noted above, a predetermined number of ATP sequences may be delivered. In a preferred embodiment, only a single ATP therapy sequence is delivered to minimize therapy delivery time. The ATP therapy may be delivered in burst, ramp, ramp-plus-pacing, or any of the other ATP therapy delivery modes known in the art.

Sometime after ATP delivery is complete, capacitor charging is also completed. At this time, or at a time determined by the optional programmable value "Time_to_Shock", confirmation is initiated (416). At substantially the same time, or, in an alternative embodiment, at a predetermined time thereafter, synchronization is initiated (418). If confirmation determines that the arrhythmia has been terminated (420), shock delivery is aborted and processing is complete (424), as indicated by arrow 423. Otherwise, shock delivery occurs upon completion of synchronization (422).

It may be noted that the ordering of the steps illustrated in FIG. 11 are exemplary, and may be changed. For example, the ordering of steps 406 through 410 may be changed without altering the scope of invention. Moreover, some of the steps may be omitted. For example, in one embodiment, one or more of steps 406 and 408 or 410 and 412 may be omitted. Other modifications to the method are possible within the scope of the present invention.

The preceding specific embodiments are illustrative of the practice of the invention. It is to be understood, therefore, that other expedients known to those of skill in the art or disclosed herein may be employed without departing from the invention or the scope of the appended claim. The Specification is therefore to be considered as exemplary in nature, with the scope of the invention defined by the following claims.

What is claimed is:

1. A system for treating an arrhythmia of a heart, comprising:
   a first output circuit to deliver anti-tachy pacing (ATP) pulses to the heart;
   a second output circuit to deliver a high-voltage shock; and
   a control circuit coupled to the first and second output circuits to control delivery of the ATP pulses relative to delivery of the high-voltage shock based on an adjustable parameter, wherein the control circuit includes a circuit to prevent delivery of ATP pulses from impacting a time of delivery of the high-voltage shock and a circuit to control delivery of ATP pulses based on a programmed energy level of the high-voltage shock.

2. The system of claim 1, wherein the second output circuit includes at least one capacitor, and wherein the control circuit includes means for calculating a time required to charge the at least one capacitor based on the programmed energy level of the high-voltage shock.

3. The system of claim 2, wherein the second output circuit includes a battery, and wherein the control circuit includes means for adjusting the estimated time required to charge the at least one capacitor based on life of the battery.

4. The system of claim 3, wherein the control circuit includes means for controlling a length of time for delivering ATP pulses based on the time required to charge the at least one capacitor.

5. The system of claim 1, wherein the control circuit includes means for controlling delivery of the ATP pulses based on a first parameter that determines the amount of time for delivering the ATP pulses.

6. The system of claim 5, wherein the control circuit includes means for controlling delivery of the ATP pulses based on a second parameter that determines an amount of time for determining whether the arrhythmia terminated.

7. The system of claim 6, wherein the control circuit includes means for disabling delivery of the ATP pulses if the sum of the first parameter and the second parameter are greater than the time required to charge the at least one capacitor.

8. The system of claim 6, wherein at least one of the first parameter and the second parameter is programmable.

9. The system of claim 1, wherein the control circuit includes confirming means for detecting whether the arrhythmia has terminated, and wherein the confirming means begins detection prior to the at least one capacitor being charged to the programmed energy level.

10. The system of claim 1, wherein the control circuit includes confirming means for detecting whether the arrhythmia has terminated, and wherein the confirming means performs detection after the at least one capacitor is charged to the programmed energy level.

11. The system of claim 9, wherein the control circuit includes means for synchronizing the second output circuit to deliver a high-voltage shock synchronized with cycles of the heart, and wherein at least a portion of the synchronizing is performed at the same time the confirming means is performing detection.

12. The system of claim 10, wherein the control circuit includes means for synchronizing the second output circuit to deliver a high-voltage shock synchronized with cycles of the heart, and wherein at least a portion of the synchronizing is performed at the same time the confirming means is performing detection.

13. A system for treating an arrhythmia of a heart, comprising:
   a first output circuit to deliver anti-tachy pacing (ATP) pulses to the heart;
   a second output circuit to deliver a high-voltage shock; and
   a control circuit coupled to the first and second output circuits to control delivery of the ATP pulses relative to delivery of the high-voltage shock based on an adjustable parameter, wherein the control circuit includes a circuit to prevent delivery of ATP pulses from impacting a time of delivery of the high-voltage shock, and wherein the control circuit includes means for synchronizing the second output circuit to deliver a high-voltage shock synchronized with cycles of the heart, and wherein the control circuit includes means for controlling delivery of the high-voltage shock based on a programmable Time_to_Shock parameter that determines a period of time substantially from detection of the arrhythmia to a time the synchronizing is initiated.

14. A method of treating an arrhythmia of the heart, comprising:
   a.) detecting the arrhythmia;
   b.) controlling delivery of anti-tachy pacing (ATP) pulses to the heart based on at least one programmable parameter; and
   c.) controlling delivery of a high-voltage shock to the heart based on the at least one programmable parameter in a manner that ensures that a time of delivery of the high-voltage shock is unaffected by the delivery of the ATP pulses, wherein step b.) includes controlling delivery of ATP pulses based on a programmed shock energy of the high-voltage shock.

15. The method of claim 14, wherein step b.) includes using a programmed shock energy to determine a capacitor charging time.

16. The method of claim 14, wherein step b.) includes controlling delivery of the ATP pulses based, at least in part, on a first parameter indicating time available for the delivery of the ATP pulses.

17. The method of claim 16, wherein step b.) includes controlling the delivery of the ATP pulses based, at least in part, on a second parameter indicating a time period for confirming whether the arrhythmia was terminated.

18. The method of claim 17, wherein the delivery of the ATP pulses is disabled if the sum of the first and the second parameters is greater than the time available for the delivery of the ATP pulses.

19. The method of claim 18, wherein at least one of the first parameter and the second parameter is programmable.

20. The method of claim 19, wherein the method is performed by an implantable medical device including a battery, and wherein step b.) includes adjusting the capacitor charging time based on a lifetime of the battery.

21. The method of claim 20, wherein step b.) includes adjusting at least one of the first parameter and the second parameter based, at least in part, on the adjusted capacitor charging time.

22. The method of claim 18, wherein at least one of the first parameter and the second parameter is a predetermined minimum system value.

23. The method of claim 16, wherein step c.) includes synchronizing delivery of the high-voltage shock to a rhythm of the heart, and wherein step b.) includes controlling the delivery of the ATP pulses based, at least in part, on a second parameter indicating a time period extending substantially from detection of the arrhythmia to initiation of the synchronizing of delivery of the high-voltage shock.

24. The method of claim 16, further comprising the step of confirming whether the arrhythmia was terminated.

25. The method of claim 24, wherein the step of confirming whether the arrhythmia is terminated is performed after expiration of the capacitor charging time.

26. The method of claim 24, wherein the step of confirming whether the arrhythmia is terminated is initiated before expiration of the capacitor charging time.

27. The method of claim 25, wherein step c.) includes synchronizing delivery of the high-voltage shock to a rhythm of the heart.

28. The method of claim 26, wherein step c.) includes synchronizing delivery of the high-voltage shock to a rhythm of the heart.

29. The method of claim 27, wherein a portion of the time for confirming whether the arrhythmia was terminated is performed while synchronizing delivery of the high-voltage shock.

30. The method of claim 28, wherein a portion of the time for confirming whether the arrhythmia was terminated is performed while synchronizing delivery of the high-voltage shock.

31. The method of claim 25, wherein the step of confirming whether the arrhythmia is terminated is performed substantially until the time of delivery of the high-voltage shock.

32. The method of claim 26, wherein the step of confirming whether the arrhythmia is terminated is performed substantially until the time of delivery of the high-voltage shock.

33. A system for treating an arrhythmia of a heart, comprising:
   a first output circuit to deliver anti-tachy pacing (ATP) pulses to the heart;
   at least one capacitor to store a high-voltage shock;
   a second output circuit to deliver the high-voltage shock stored by the capacitor subsequent to a charge-time for charging the at least one capacitor and a synchronization period for synchronizing delivery of the high-voltage shock;
   a control circuit coupled to the first and second output circuits to control delivery of the ATP pulses relative to delivery of the high-voltage shock based on an adjustable parameter; and
   sensor processing circuitry determining whether the ATP pulses successfully treat the arrhythmia during a confirmation period, wherein the charge-time for charging the at least one capacitor terminates at a charge time end and wherein the confirmation period and the synchronization period are initiated subsequent to the charge time end.

34. The system of claim 33, wherein the confirmation period occurs simultaneously with the synchronization period.

35. The system of claim 33, wherein the synchronization period is initiated subsequent to completion of the confirmation period and the sensor processing circuitry determines the ATP pulses have not successfully treated the arrhythmia.

36. The system of claim 33, wherein the synchronization period is initiated subsequent to initiation of the confirmation period.

37. The system of claim 33, wherein the adjustable parameter is a programmable time-to-shock period and wherein the synchronization period and the confirmation period are initiated subsequent to the time-to-shock period.

38. The system of claim 37, wherein expiration of the time-to-shock period initiates the confirmation period and the synchronization period is initiated at a predetermined time subsequent to the initiation of the confirmation period.

39. The system of claim 38, wherein the synchronization period is initiated during the confirmation period.

40. The system of claim 38, wherein the synchronization period is initiated subsequent to the confirmation period.

41. The system of claim 37, wherein the programmable time-to-shock period corresponds to a programmable number of beats.

42. The system of claim 37, wherein the programmable time-to-shock period corresponds to a predetermined time period.

43. The system of claim 37, wherein the first output circuit delivers the ATP pulses for a first time period, and the sum of the first time period and the confirmation period is less than the programmable time-to-shock period.

44. A system for treating an arrhythmia of a heart, comprising:

a first output circuit to deliver anti-tachy pacing (ATP) pulses to the heart;

a second output circuit to deliver a high-voltage shock; and a control circuit coupled to the first and second output circuits to control delivery of the ATP pulses relative to delivery of the high-voltage shock, the control circuit includes means for controlling delivery of the ATP pulses based on a first parameter that determines the amount of time for delivering the ATP pulses.

45. The system of claim 44, wherein the control circuit includes means for controlling delivery of the ATP pulses based on a second parameter that determines an amount of time for determining whether the arrhythmia terminated.

46. The system of claim 45, wherein the control circuit includes means for disabling delivery of the ATP pulses if the sum of the first parameter and the second parameter are greater than the time required to charge the at least one capacitor.

47. The system of claim 45, wherein at least one of the first parameter and the second parameter is programmable.

48. The system of claim 44, wherein the second output circuit includes at least one capacitor, and wherein the control circuit includes means for calculating a time required to charge the at least one capacitor based on the programmed energy level of the high-voltage shock.

49. The system of claim 48, wherein the second output circuit includes a battery, and wherein the control circuit includes means for adjusting the estimated time required to charge the at least one capacitor based on life of the battery.

50. The system of claim 48, wherein the control circuit includes means for controlling a length of time for delivering ATP pulses based on the time required to charge the at least one capacitor.

* * * * *